(12) United States Patent
Turner et al.

(10) Patent No.: US 11,432,781 B2
(45) Date of Patent: Sep. 6, 2022

(54) THREE DIMENSIONAL X-RAY IMAGING SYSTEM

(71) Applicant: 3DIO, INC.

(72) Inventors: D. Clark Turner, Payson, UT (US); Douglas P. Hansen, Spanish Fork, UT (US); Thomas L. Youd, Holladay, UT (US)

(73) Assignee: 3DIO, Inc., Orem, UT (US)

( * ) Notice: Subject to any disclaimer, the term of this patent is extended or adjusted under 35 U.S.C. 154(b) by 43 days.

(21) Appl. No.: 16/610,203

(22) PCT Filed: May 3, 2018

(86) PCT No.: PCT/US2018/030970
§ 371 (c)(1),
(2) Date: Nov. 1, 2019

(87) PCT Pub. No.: WO2018/204705
PCT Pub. Date: Nov. 8, 2018

(65) Prior Publication Data
US 2020/0345318 A1    Nov. 5, 2020

Related U.S. Application Data

(60) Provisional application No. 62/500,914, filed on May 3, 2017.

(51) Int. Cl.
*A61B 6/00*        (2006.01)
*A61B 6/14*        (2006.01)
(Continued)

(52) U.S. Cl.
CPC .............. *A61B 6/145* (2013.01); *A61B 6/025* (2013.01); *A61B 6/4452* (2013.01); *A61B 6/486* (2013.01); *A61B 6/0478* (2013.01); *A61B 6/582* (2013.01)

(58) Field of Classification Search
CPC ....... A61B 6/145; A61B 6/025; A61B 6/4452; A61B 6/486; A61B 6/14
See application file for complete search history.

(56) References Cited

U.S. PATENT DOCUMENTS 4,247,780 A    1/1981   Webber et al.
5,109,276 A    4/1992   Nudelman et al.
(Continued)

FOREIGN PATENT DOCUMENTS

CN    101983034 A    3/2011
CN    105873516 A    8/2016
(Continued)

OTHER PUBLICATIONS

Richard Webber: See sub-article, Three-Dimensional Image Display of Dental Structures https://pdfs.semanticscholar.org/083f/c4f9f814a60624d859b645b2750eca979858.pdf (Last accessed Mar. 2, 2020).

(Continued)

*Primary Examiner* — Dani Fox
(74) *Attorney, Agent, or Firm* — Kenneth E. Horton; Barnes & Thornburg LLP

(57) ABSTRACT

Three dimensional x-ray imaging systems are described in this application. In particular, this application describes a 3D dental intra-oral imaging (3DIO) system that collects a series of 2D image projections. The x-ray imaging system comprises a housing, an x-ray source attached to a articulating or motion gantry configured to move the source within the housing to multiple positions, an x-ray detector array located on an opposite side of an object to be imaged from the x-ray source, where the detector array is synchronized with the x-ray source to capture 2D images of the object when the x-ray source is located in multiple imaging positions, and a processor configured to accept the 2D images and reconstruct a 3D image. The multiple imaging positions (Continued)

can be located on a plane substantially parallel to the x-ray detector array. Other embodiments are described.

21 Claims, 9 Drawing Sheets

(51) Int. Cl.
*A61B 6/02* (2006.01)
*A61B 6/04* (2006.01)

(56) References Cited

U.S. PATENT DOCUMENTS

| | | | |
|---|---|---|---|
| 5,200,819 A | 4/1993 | Nudelman et al. |
| 5,200,838 A | 4/1993 | Nudelman et al. |
| 5,668,844 A | 9/1997 | Webber |
| 6,196,715 B1 | 3/2001 | Nambu et al. |
| 6,549,607 B1 | 4/2003 | Webber |
| 6,801,597 B2 | 10/2004 | Webber |
| 6,810,278 B2 | 10/2004 | Webber et al. |
| 6,885,724 B2 | 4/2005 | Li et al. |
| 6,980,624 B2 | 12/2005 | Li et al. |
| 7,110,807 B2 | 9/2006 | Webber et al. |
| 7,751,528 B2 | 7/2010 | Zhou et al. |
| 7,801,587 B2 | 9/2010 | Webber et al. |
| 7,813,469 B2 | 10/2010 | Siltanen et al. |
| 8,126,112 B2 | 2/2012 | Massie et al. |
| 8,284,894 B2 | 10/2012 | Poorter |
| 9,036,776 B2 | 5/2015 | Sadakane et al. |
| 9,113,799 B2 | 8/2015 | Katsumata et al. |
| 9,144,406 B2 | 9/2015 | Dennerlein |
| 9,148,566 B2 | 9/2015 | Wagatsuma |
| 9,208,559 B1 | 12/2015 | Maschke |
| 9,351,701 B2 | 5/2016 | Yamakawa et al. |
| 9,408,579 B2 | 8/2016 | Yamakawa et al. |
| 9,427,286 B2 | 8/2016 | Siewerdsen et al. |
| 9,544,577 B2 | 1/2017 | Blassnig et al. |
| 9,629,590 B2 | 4/2017 | Katsumata et al. |
| 9,636,183 B2 | 5/2017 | Helm et al. |
| 9,668,705 B2 | 6/2017 | Tamakawa et al. |
| 9,700,740 B2 | 7/2017 | Maurer, Jr. |
| 9,713,505 B2 | 7/2017 | Helm et al. |
| 9,730,776 B2 | 8/2017 | Lal et al. |
| 9,743,893 B2 | 8/2017 | Inglese et al. |
| 9,782,136 B2 | 10/2017 | Zhou et al. |
| 9,795,348 B2 | 10/2017 | Ruijters |
| 9,855,013 B2 | 1/2018 | Morita et al. |
| 9,872,663 B2 * | 1/2018 | Duewer ............ A61B 6/5252 |
| 9,888,893 B2 | 2/2018 | Hoernig |
| 9,898,840 B2 | 2/2018 | Klausz et al. |
| 9,901,309 B2 | 2/2018 | Defreitas et al. |
| 9,901,315 B2 | 2/2018 | Farbizio et al. |
| 9,907,516 B2 | 3/2018 | Litzenberger et al. |
| 9,907,520 B2 | 3/2018 | Zhou et al. |
| 10,039,508 B2 | 8/2018 | Abramovich |
| 2003/0235265 A1 | 12/2003 | Clinthorne et al. |
| 2012/0328071 A1 | 12/2012 | Katsumata et al. |
| 2014/0093032 A1 | 4/2014 | Dennerlen |
| 2015/0131774 A1 | 5/2015 | Maurer, Jr. et al. |
| 2015/0265237 A1 | 9/2015 | Keeve et al. |
| 2016/0220212 A1 | 8/2016 | Duewer |
| 2016/0317107 A1 * | 11/2016 | Zhou .............. A61B 6/025 |
| 2017/0038484 A1 | 2/2017 | Cox |

FOREIGN PATENT DOCUMENTS

| | | |
|---|---|---|
| GB | 2533801 A | 7/2016 |
| JP | H10295680 A | 11/1998 |
| JP | 2005013738 A | 1/2005 |
| JP | 2006034451 A | 2/2006 |
| JP | 2015144898 A | 8/2015 |
| KR | 20120010639 A | 2/2012 |
| KR | 20140087207 A | 7/2014 |
| WO | 2017021520 A1 | 2/2017 |
| WO | 2017196413 A1 | 11/2017 |

OTHER PUBLICATIONS

Srinivasan Vedantham, PhD, Digital Breast Tomosynthesis: State of the Art https://pubs.rsna.org/doi/10.1148/radiol.2015141303 (Last accessed Mar. 2, 2020).
http://www.rsna.org/News.aspx?id=17933 (last accessed Mar. 2, 2020).
https://radiologykey.com/computed-tomography-7/ (Last accessed Mar. 2, 2020).
Yakimovsky and Cunningham entitled "A System for Extracting Three Dimensional Measurements from a Stereo Pair of TV Cameras", published in Computer Graphics and Image Processing 7, p. 195-210, 1978.
Guohua Cao, et al. "A Stationary-Sources and Rotating-Detectors Computed Tomography Architecture for Higher Temporal Resolution and Lower Radiation Dose", EEE Access, Jan. 2014.
Abreu, M Jr et al. "Influence of the number of basis images and projection array on caries detection using tuned aperture computed tomography (TACT)." Dento maxillo facial radiology vol. 31,1 (2002): 24-31. doi:10.1038/sj/dmfr/4600656.

* cited by examiner

THREE DIMENSIONAL X-RAY IMAGING SYSTEM

FIELD

This application relates generally to X-ray equipment. More specifically, this application relates to x-ray devices and systems that are used for three dimensional imaging.

X-ray imaging systems typically contain an X-ray source and an X-ray detector. X-rays (or other types of radiation used for imaging) are emitted from the source and impinge on the X-ray detector to provide an X-ray image of the object or objects that are placed between the X-ray source and the detector. The X-ray detector is often an image intensifier or even a flat panel digital detector.

BACKGROUND

X-ray imaging systems typically contain an X-ray source and an X-ray detector. X-rays (or other types of radiation used for imaging) are emitted from the source and impinge on the X-ray detector to provide an X-ray image of the object or objects that are placed between the X-ray source and the detector. The X-ray detector is often an image intensifier or even a flat panel digital detector.

Intra-oral radiography is a standard imaging technique in dentistry, with bite-wing and periapical x-rays considered a standard of care in dental practice. However, there are many features of the tooth anatomy that are not visible in standard intra-oral radiographs as these are 2D projections of a 3D structure. Additionally, while bite-wing radiographs are very good at detecting interproximal caries, a slight variation in angle may serve to obscure the proper diagnosis due to overlapping with adjacent teeth or other factors. Tooth fractures and/or small cracks are not visible in radiographs unless the image projection angle is coincidentally aligned with the crack direction. For endodontics, curvature of the roots is not always visible because radiographs show only the projection and not the true length or vector of the root. In some cases, extra or accessory canals aren't visible if overlapped in the 2D image. Radiographs are also used for implant planning. While cone-beam computed tomography (CBCT) is often used for implant planning, the majority of implants are for a single tooth. Therefore the patient is receiving a high relative dose by performing a CBCT scan of the entire oral cavity, when 3D image information is needed for only a single tooth.

SUMMARY

This application relates generally to three dimensional (3D) x-ray imaging systems. In particular, this application describes a 3D dental intra-oral imaging (3DIO) system that collects a series of 2D image projections. The x-ray imaging system comprises a housing, an x-ray source attached to a articulating or motion gantry configured to move the source within the housing to multiple positions, an x-ray detector array located on an opposite side of an object to be imaged from the x-ray source, where the detector array is synchronized with the x-ray source to capture 2D images of the object when the x-ray source is located in multiple imaging positions, and a processor configured to accept the 2D images and reconstruct a 3D image. The multiple imaging positions can be located on a plane substantially parallel to the x-ray detector array.

The imaging system can make a three dimensional image of an object by providing an x-ray source on a motion gantry configured to position the source within a housing located on a side of an object to be imaged, positioning an x-ray detector array on an opposite side of the object, moving the x-ray source to multiple positions in the housing that are located on a plane substantially parallel to the x-ray detector array, collecting multiple 2D images of the object when the x-ray source is located in the multiple positions; and reconstructing a 3D image using the multiple 2D images.

These x-ray systems and methods offer a quick method of imaging an object, such as a tooth, while at the same time using a low radiation dose.

BRIEF DESCRIPTION OF THE DRAWINGS

The following description can be better understood in light of the Figures which show various embodiments and configurations of the imaging systems.

Figure 1:
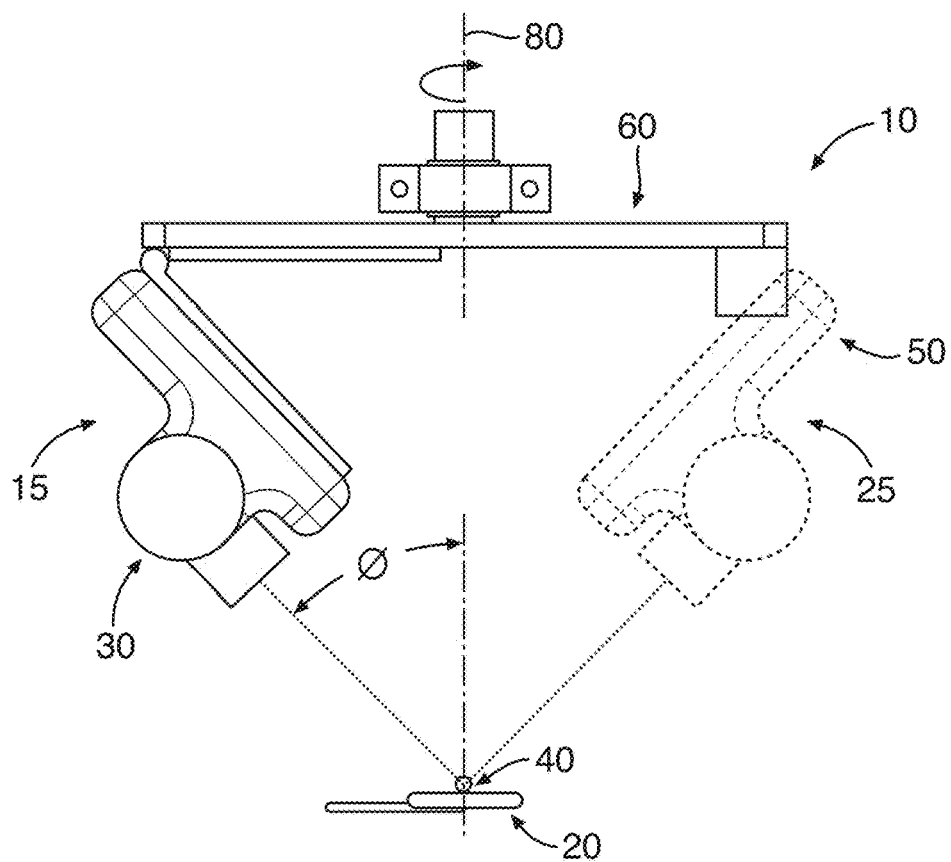
FIG. 1 shows a view of some embodiments of a 3DIO imaging system.
Figure 2:
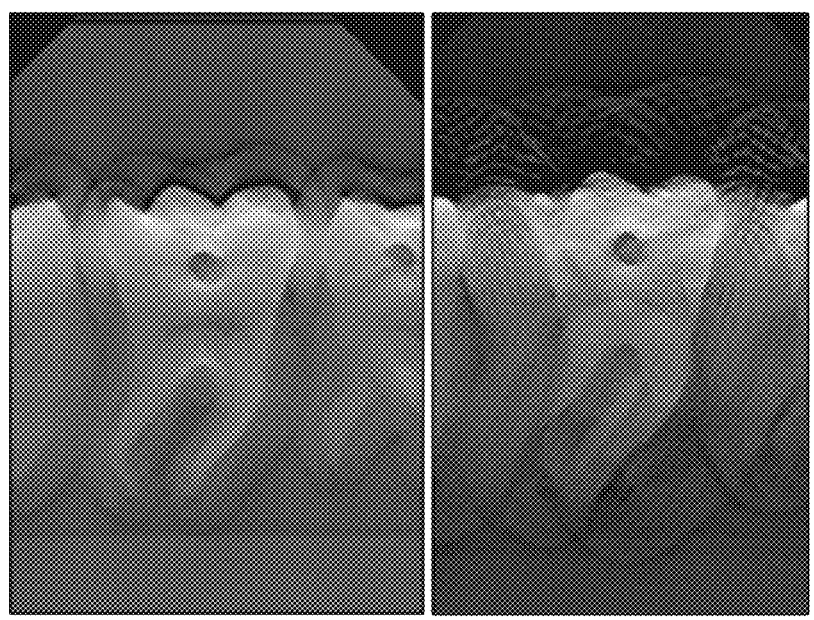
FIG. 2 shows another view of some embodiments of images produced by a 3DIO imaging system with sample 3D slices at a plane chosen to demonstrate high contrast between the simulated carie and the surrounding tooth. The left image is taken at a 15 degree cone angle and the right images at a 30 degree cone angle. The image defects due to z-plane artifacts can be seen in the right image.

Together with the following description, the Figures demonstrate and explain the principles of the structures and methods described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described X-ray systems can be implemented and used without employing these specific details. Indeed, the described systems and methods can be placed into practice by modifying the described systems and methods and can be used in conjunction with any other apparatus and techniques conventionally used in the industry. For example, while the description below focuses on imaging systems for dental imaging, they can be used for other purposes such as medical imaging, veterinary imaging, industrial inspection applications, and anywhere where x-ray radiography equipment is currently being used to generate a standard 2D x-ray image.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Current 2D radiographs of objects (such as a tooth of a patient) are often ambiguous for detection of problems or defects because they are not usually able to visualize fractures in a tooth, and because they use plane projections, they can miss tooth curvature and other anomalies important to dental diagnosis and treatment. So cone-beam computed tomography (CBCT) is becoming widely used in dentistry instead of 2D radiographs. In CBCT, a patient's head is positioned in-between a large imaging detector and an opposing x-ray source. The detector and source rotate around the head while taking multiple 2D images. Using these 2D images, a 3D image of the patient's oral and maxillofacial anatomy can be reconstructed. This technique works very well for imaging the entire oral cavity and displaying the spatial relationships between the teeth and other bony structures located in the head of a patient. The CBCT technique is, therefore, often used for dental implants and orthodontic procedures where such spatial relationships are important.

However, projecting x-rays through the entire head, as required in CBCT procedures, leads to high x-ray scattering and attenuation from non-resolving anatomy. This can result in spatial resolution in the CBCT image that is much worse than intra-oral radiography using 2D radiographs with an intra-oral sensor positioned right next to the tooth of interest. In addition, the patient dose in CBCT procedures is considerably higher than in intra-oral radiography using 2D radiographs. This situation is particularly concerning since most orthodontic procedures are performed on children who are more susceptible than adults to radiation damage. And CBCT procedures are not often used to image a single tooth, or just a few teeth, due to the high radiation dose. Thus, CBCT is not an effective and safe imaging tool for the majority of dental procedures which only involve a single tooth or a few teeth.

Recognizing the limitations of CBCT procedures and 2D radiographs, the systems described herein use intra-oral imaging techniques that can be presented as a high resolution 3D image. These 3DIO (three dimensional, intra-oral) systems provide a simple 3D imaging technique that provides a 3D high resolution image using 2D radiographs taken at a low radiation dose.

Some embodiments of a 3DIO system are illustrated in FIGS. 1-11. FIG. 1 shows the geometry of the 3DIO systems with a rotation scheme shown with the x-ray source at position 15 and position 25 around axis of rotation 80. In FIG. 1, the 3DIO system 10 comprises an imaging detector 20 located inside the mouth and relatively stationary adjacent to the tooth (or teeth) 40 of a patient. The 3DIO system 10 also contains an x-ray source 30 that is located within a housing 50. The housing 50 can be connected to a support arm 60.

The 3DIO system 10 can contain any X-ray source 30 and X-ray detector 20 that allows the system 10 to take multiple 2D x-ray images or radiographs. The X-ray source 30 can contain any source that generates and emits X-rays, including a standard stationary anode X-ray source, micro-focus x-ray source, rotating anode x-ray source, and/or a fluoroscopic X-ray source. In some embodiments, the x-ray source can operate with about 40 to about 90 kV and from about 1 to about 10 mA. In other embodiments, the x-ray source can operate with about 75 kV and about 2 mA. In some embodiments, the X-ray source and X-ray detector can be made modular so that different sizes and types of X-ray sources and X-ray detectors can be used.

The X-ray detector 20 can contain any detector that detects X-rays, including an image intensifier, CMOS camera, and/or a digital flat panel detector. In some configurations, the detector can have a substantially square shape with a length ranging from about 20 cm to about 30 cm. In other configurations, though, the x-ray detector 20 does not need to have a substantially square shape.

In some configurations, the x-ray detector 20 is synchronized with the X-ray source 30. Thus, the x-ray detector is activated substantially at the same time that the x-ray source is activated, thereby capturing a 2D-projection image generated by the x-ray radiation passing through the patient's tooth/teeth and onto the detector.

In some configurations, the X-ray detector 20 can have quick readout speed. In the 3DIO systems described herein, this read-out speed can range from about 5 to about 6 frames per second. This quick speed allows the necessary number of frames to be taken in a reasonable period of time. In other embodiments, the detector read out speed can be more than 10 frames per second. In yet other embodiments, the detector read out speed can be more than 20 frames per second. In still other embodiments, the detector read out speed can be about 30 frames per second.

In some embodiments, the number of pixels in the x-ray detector needs to be limited to a reasonable number, such as within the range of 100,000 to 190,000 pixels. More pixels require not only a slightly longer read-out time, but also add more complexity to the reconstruction algorithm used to render the 3D image from the 2D images. But the number of pixels in the detector can be kept within this range because of the size constraints imposed by the need to fit into the patient's mouth, as well as reducing the complexity of the math required to reconstruct the image. Consequently in these embodiments, only 2 to 3 teeth can be adequately imaged because of the size of the detector.

Figure 9:
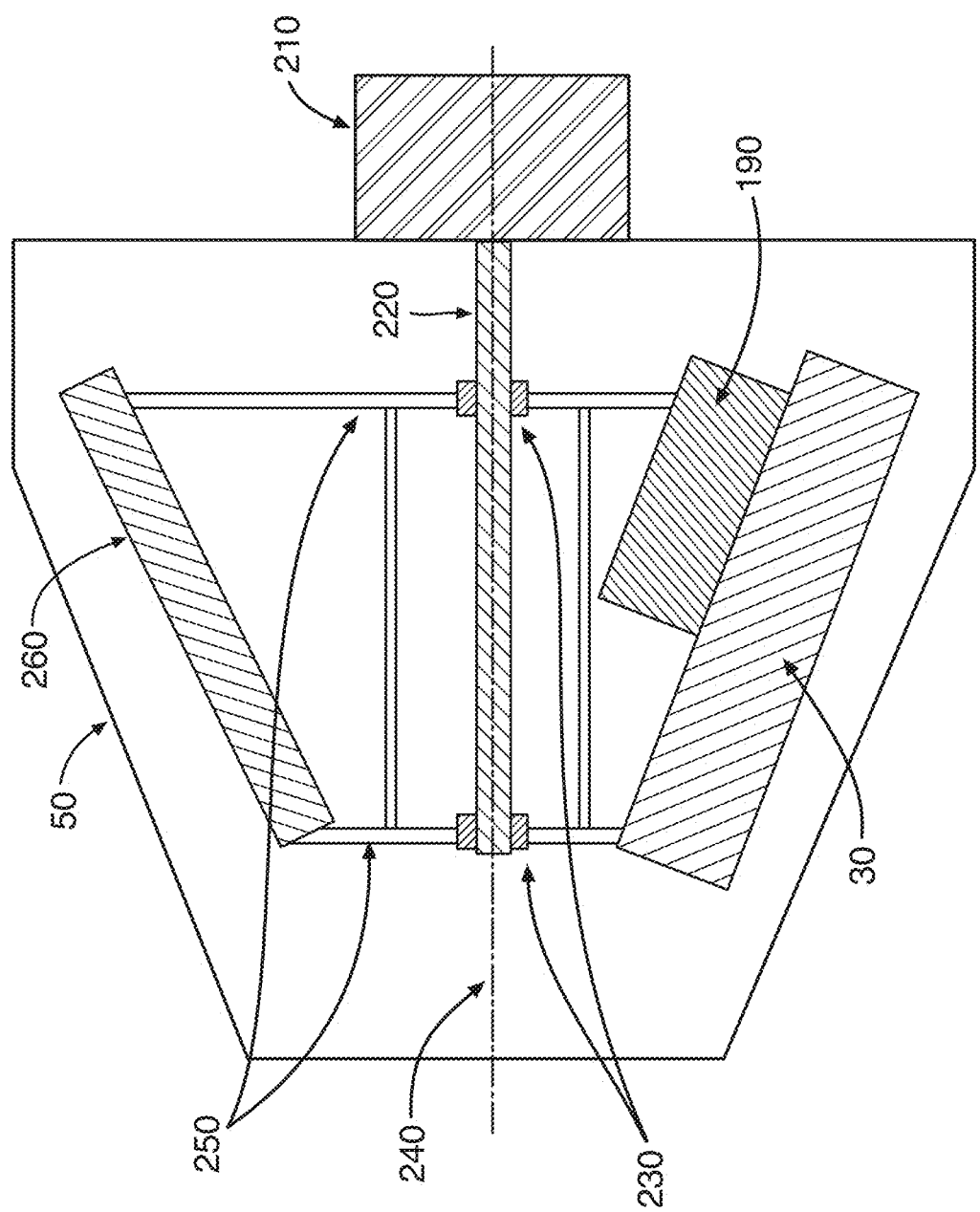
FIG. 9 shows some embodiments of the housing and components contained in the housing of a 3DIO imaging system.

As shown in detail in FIG. 9, the X-ray source 30 can be contained in housing 50. The housing 50 can be configured with a first part enclosing the x-ray source 30 as shown in FIG. 9. The housing 50 also encloses a second part that contains a counterweight 260 for the X-ray source 30, power electronics 190, and other components and which facilitates smooth vibration-free rotary motion of the source 30. The x-ray source 30 and its associated power electronics 190 and the counterweight 260 are located on substantially opposite sides of rotating mechanical assembly 250 which supports the x-ray source 30, the power electronics 190, counterweight 260, and other components (not shown). The rotating mechanical assembly 250 is mounted to axle 220 (or other mechanical device to support the mechanical assembly) with an axis of rotation 240 using the bearings and/or electric motor assembly 230 to enable drive rotation of the mechanical assemble 250.

As shown in FIG. 9, the housing 50 can be configured so that it is a single part that encloses both the X-ray source 30 and these components. In other configurations, the housing can be separated into different parts to contain the x-ray source 30 and other components. As shown in FIG. 9, the electronic components for control and power conditioning 210 can be located just outside of the housing 50. In other embodiments, these electronic components 210 can be located on the support arm or other convenient location. In yet other embodiments, these electronic components 210 can be located internal to the housing 50.

Figure 10:
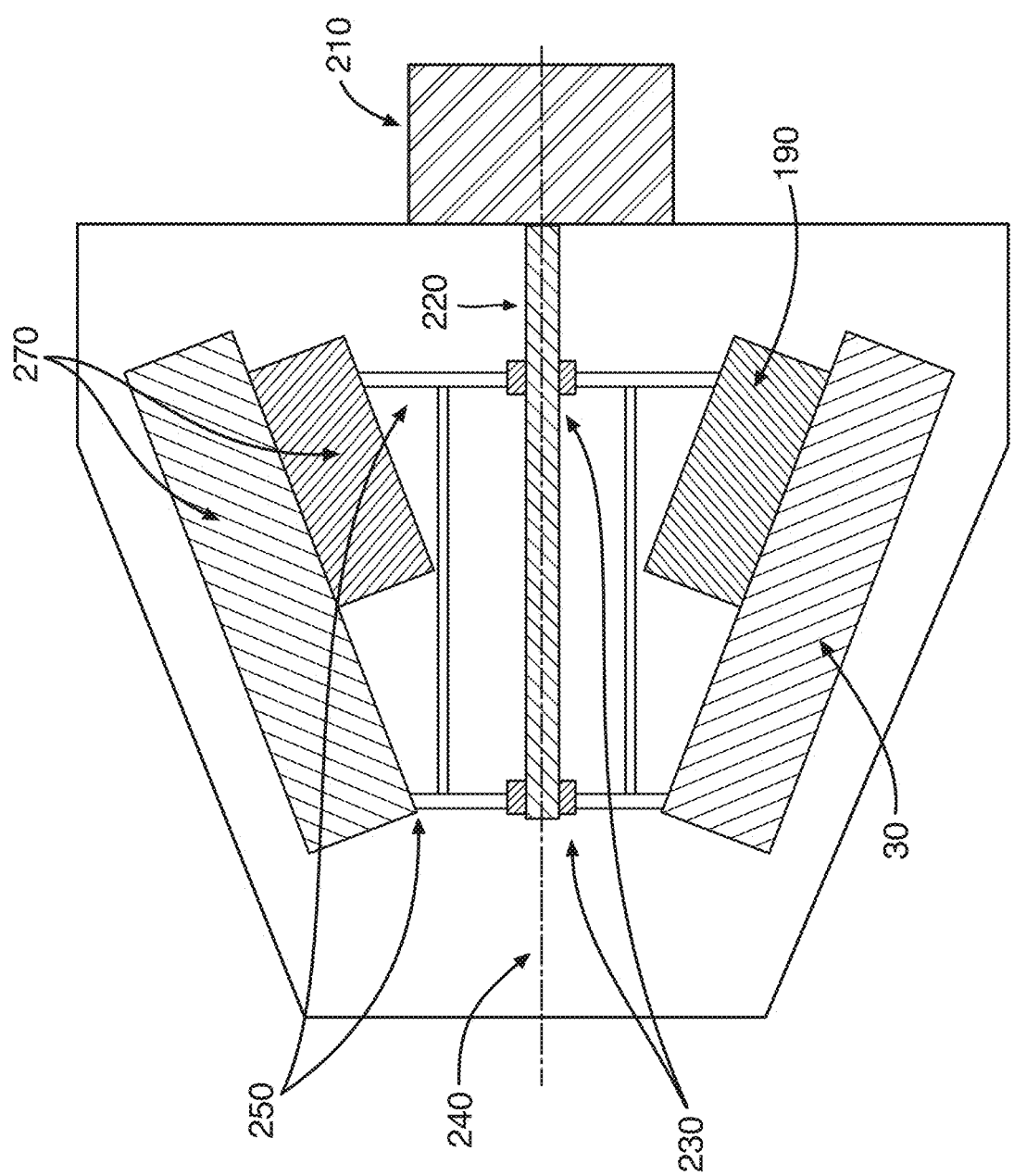
FIG. 10 illustrates some embodiments of using multiple x-ray sources in the housing a 3DIO imaging system.

In some embodiments, multiple x-ray sources can be used in the 3DIO systems. In these embodiments, as shown in FIG. 10, multiple x-ray sources (30, 270) would enable a reduction in the mechanical rotation speed required to cover all of the desired source positions needed to generate the 3D image. These sources could be fired in an alternating manner or otherwise as required to obtain all of the desired 2D images from the various x-ray source locations within the head. The remainder of the components in FIG. 10 can be similar to those shown in FIG. 9, with the exception that the second x-ray source and its associated high voltage electronics 270 have replaced the counterweight 260.

The use of multiple sources 30 within the housing 50 would also provide the benefit of reduced motion blur in the x-ray images obtained since the x-ray source is moving at a lower velocity than would be required with a single source. The use of multiple substantially identical sources 30 would also negate the requirement for a counterweight since the multiple sources can be positioned to result in a balanced rotational system. More than the two x-ray sources could be incorporated into the 3DIO system, with the full 360 degrees of the circle being divided by the number of sources used so that the multiple sources are distributed evenly around the circular frame on which they are mounted. Of course, the use of multiple sources will increase the system over-all cost and complexity, so the needs and constraints of the intended use will need to be considered in choosing the number of sources to be included within a particular 3DIO system.

In some configurations, the 3DIO systems can contain a removable power source (such as a battery) and optionally a power supply. In these configurations, the power source and the power supply can be located internal to housing. The supporting electronics for the power source and the power supply, as well as the supporting electronics for the image display and for wireless data upload described herein, can also be located internal or external to the housing 50. Thus, in these configurations, the system 10 does not contain an external power cord. Incorporating the power source (i.e., the battery), the power supply, and the supporting electronics all within the housing 50 allows the size, weight, and external complexity of the device to be reduced. With such a configuration, the power source can easily be replaced and could deliver 60 or more x-ray images using a single charge. Of course, if needed, the 3DIO system 10 can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

The support arm 60 can have any configuration that allows the x-ray source 30 in the housing to direct x-ray beams at the desired angle through the tooth (or teeth) and on the detector 20. In the embodiments shown in FIG. 1, the support arm 60 has a substantially straight configuration with the housing 50 connected to an end thereof. In other configurations, the support arm need not be straight and can have jointed or articulated sections. In yet other configurations, the housing 50 can be connected to the support arm 60 at any location other than the end.

In other embodiments, the 3DIO system 10 also contains a frame that can be connected to the support arm 60. The frame can be configured to give a number of easy gripping options for a user during operation of the 3DIO system 10. The frame can contain one or more cross members, one or more length members, and one or more handles. The length and diameter of the various members in the frame can be changed as needed for a variety of operators. In some embodiments, the frame can be configured as a modular unit so different cross members (or length members or handles) can be used to replace the existing cross members (or length member or handles). Thus, the frame provides the ability for a user (or operator) to grip and position the 3DIO system 10 prior to operation, if desired.

The frame can also contain buttons (or triggers) that can be used to operate the 3DIO system 10. In some configurations, the 3DIO system 10 can be configured with two or more triggers. In these configurations, the triggers can be provided in multiple locations on the frame so that regardless of how the 3DIO system 10 is held in the hands of an operator, a trigger is always convenient for the operator to use. For example, the triggers can be placed on the cross members, the length members, and/or the handles. In another example, the trigger can be connected by a long cable to the rest of the 3DIO system, thereby enabling a remote triggering process. These multiple triggers make it easier to operate and easier to hold in the hand of the user when it is be used for analysis of a patient. For the triggers to operate the device, the needed internal electronics can be carried inside the frame. In other configurations, one or more of these triggers can be a remote trigger connected by a wired or wireless control. Optional button shrouds and/or compulsory push sequences can be used to prevent accidental x-ray emissions.

Figure 8:
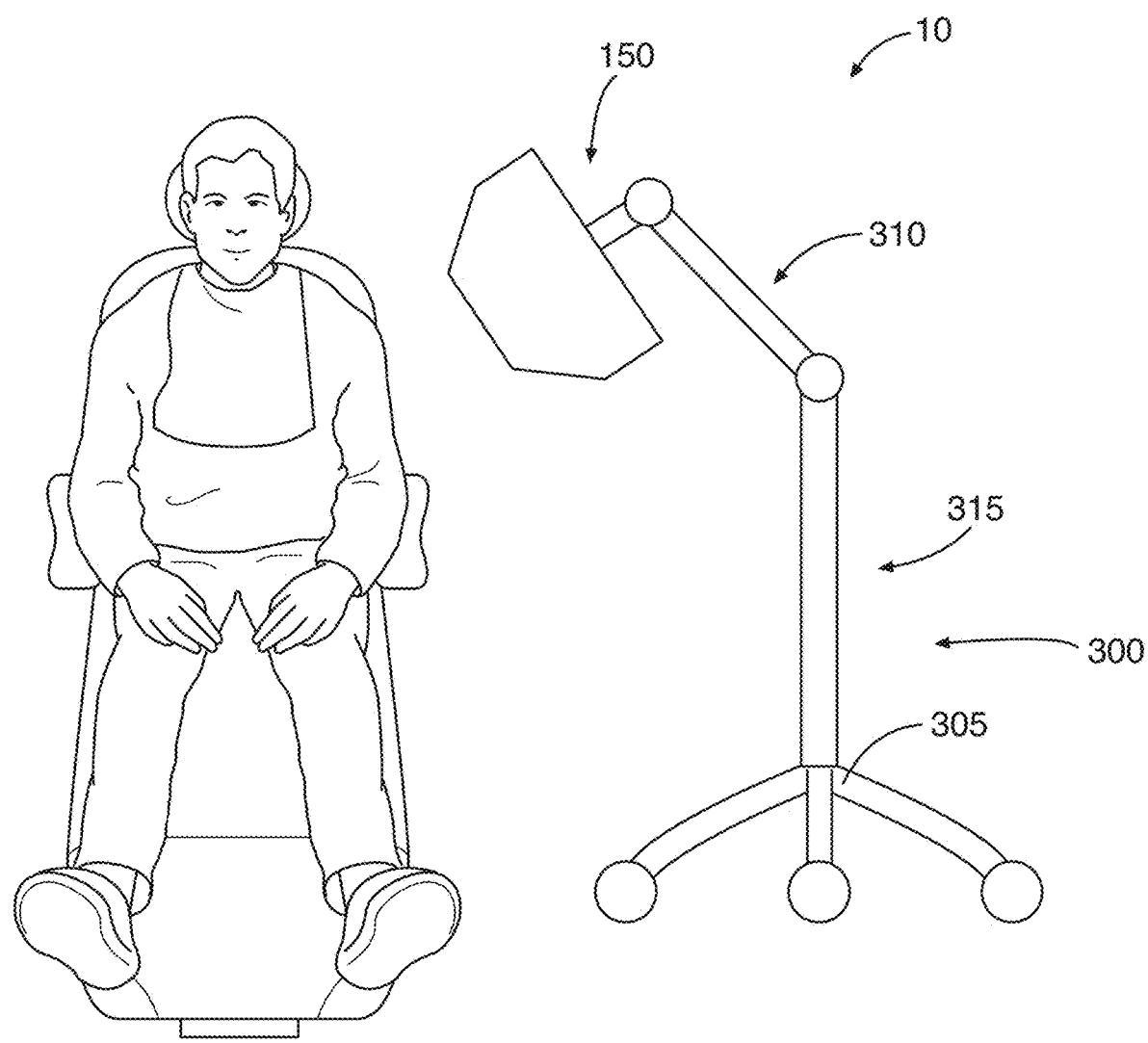

Another example of an external structure is illustrated in FIG. 8. In this Figure, the 3DIO system 10 with a frame 150 can be connected to a stand 300. The stand 300 contains a base 305 and an arm 315 extending upwards towards an extension 310. The extension 310 is connected to the joint which is, in turn, connected to the frame 150 of the 3DIO system 10. In other configurations, the 3DIO system 10 can be connected to a movable support structure. In such configurations, the movable support structure can be configured to move across a floor while supporting the 3DIO system 10. Thus, the movable support structure can comprise one or more wheels, shelves, handles, monitors, computers, stabilizing members, limbs, legs, struts, cables, and/or weights (to prevent the weight of the imaging arm and/or any other component from tipping the movable support structure). Thus, the movable support structure could comprise a wheeled structure connected to a stand that contains the joint that is connected to the frame 150 of the 3DIO system 10.

Figure 7B:
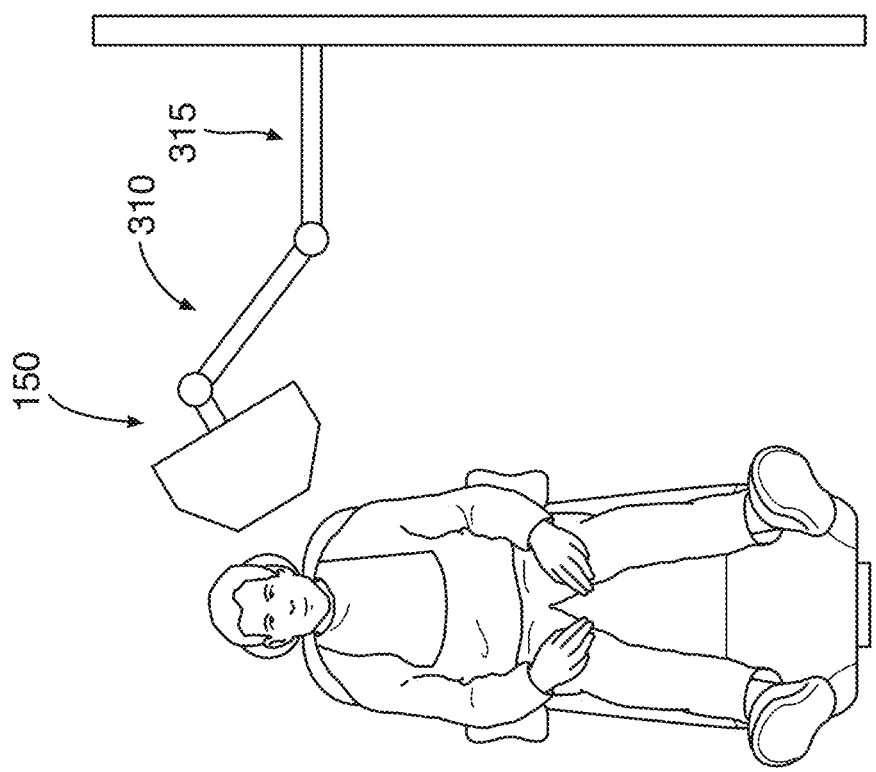
FIGS. 7A, 7B, and 8 show some embodiments of a 3DIO imaging system mounted to equipment in a dental office.
Figure 7A:
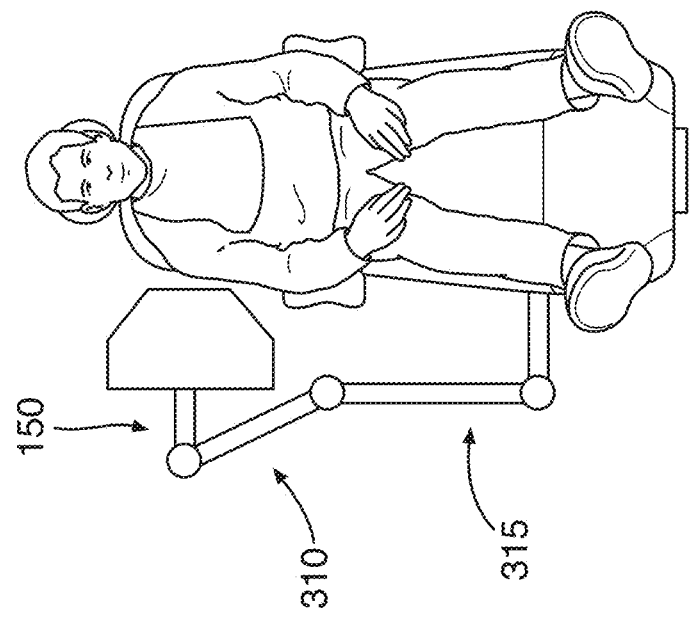

In some configurations, the 3DIO system can be mounted to a wall or a chair, as depicted in FIGS. 7A and 7B. So that it can be mounted to a wall as shown in FIG. 7B, it is desirable that the 3DIO system should fit within a rectangular volume of less than 40 cm×40 cm×60 cm and weigh less than about 5 Kg. In other configurations, the 3DIO system can be smaller than about 27 cm×27 cm×40 cm and weigh less than about 3 Kg. If it is larger or heavier than these amounts, it would be difficult to be wall mounted as shown in FIG. 7B or chair mounted as shown in FIG. 7A, it would be difficult to position for the operator, and it would increase patient anxiety.

To reduce the size and/or weight, the 3DIO systems can be equipped with small and light weight components. Over the last decade, there have been significant innovations in miniaturization of x-ray tubes. Low-power x-ray source assemblies are available that have enabled handheld x-ray devices. These light-weight sources can greatly simplify the task of motion automation for the 3DIO systems described herein. In addition, newer CMOS detectors are much more sensitive, resulting in less dose to the patient than required with conventional CCD designs. The new CMOS detectors also have very high read-out speeds allowing for rapid collection and transmission of multiple 2D images. Indeed, low-power x-ray tubes and new intra-oral CMOS detectors can be combined to achieve the same imaging efficacy achieved in some conventional tomosynthesis systems.

In some configurations, the 3DIO system 10 can comprise any suitable locking mechanism that can quickly lock and unlock the movement of the support arm 60 or the housing 50. For instance, the locking mechanism can comprise a motorized lock, an electric lock, a radio controlled lock, or cable actuated locks, etc.

The 3DIO system 10 can also contain an optional shield. The shield is used to protect an operator from backscattered x-rays when the 3DIO system is operated. The shield can accordingly be made of any radiation shielding material (including a leaded acrylic material) and shaped so that it protects the operator. The shield can be configured to be removed from the 3DIO system if needed.

The 3DIO system 10 also contains a user input/output (I/O) mechanism. In some embodiments, the I/O mechanism contains a user interface and a display that is combined in a touchscreen monitor or display. This monitor can be connected to the frame using a ball joint or any joint with multiple degrees of freedom so that the user or operator of the device can position the monitor as desired.

Figures 11A, 11B:
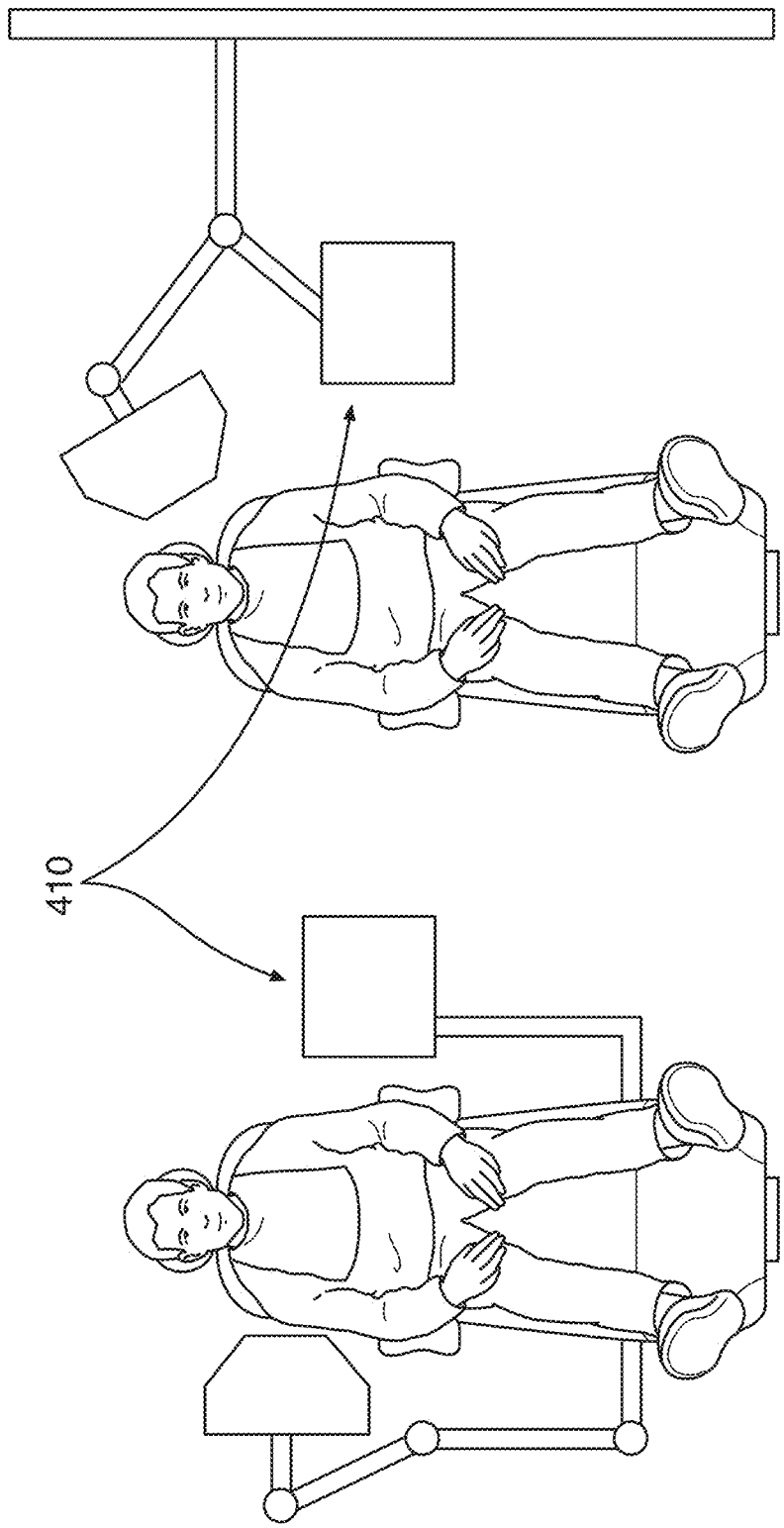
FIGS. 11A and 11B depict yet other embodiments of the 3DIO imaging systems.

The 3DIO system 10 can be controlled by an operator, such as a clinician, a doctor, a radiologist, a dentist, a technician, or other medically trained professionals and/or staff using the I/O mechanism. In some embodiments, the operator can control the 3DIO system 10 at or from a central system control, such as a system control console adjacent the device. The operator can interface with the system control through a variety of optional user interfaces integrated with the I/O mechanism, or that remain separate from the I/O mechanism. The control console, the user interface, or both 410 can be located adjacent the 3DIO system 10, as shown in FIG. 11A for a chair mounted system and FIG. 11B for a wall mounted system. In other embodiments, though, the control console and/or the user interface can be located remotely, such as in an adjacent room, so as to protect the operator from unnecessary exposure to X-rays. In still other embodiments, the display panel may be located near the patient for convenience in working with the patient, but the control console and the imaging sequence trigger may be located remotely.

In some configurations, the x-ray source 30 in the housing 50 can be shielded with a bismuth-filled (or other heavy metal) silicone material. Bismuth may be used in the radiation shielding instead of conventional lead because bismuth is considered one of the less toxic of the heavy metals, is therefore environmentally more desirable, and provides comparable radiation shielding to lead. As well, there exist a wide range of functional bismuth shielding material sources and methods for making these materials that provide increased flexibility in both design and manufacturing and allows for a greater range of function and use when compared with lead or lead-based materials. This shielding is thus very effective at preventing leakage radiation, thereby protecting the operator from radiation exposure when using the 3DIO system 10.

The effectiveness of the radiation shielding in some embodiments is dependent on the atomic number, or Z-value, and density of the shielding material. A denser shielding material with a higher Z-value is a better shielding material for high energy x-rays and gamma rays. Thus, the radiation shielding can contain other high-Z metals, such as iodine (I), barium, tin, tantalum, cesium, antimony, gold, and tungsten.

The 3DIO system can also be connected to any type of electronic device with a wired or a wireless connection. In these embodiments, the 3DIO system can contain communication cables that connect the detector to the desired electronic device, such as a computer, which can be used to analyze the x-ray images from the detector. In other embodiments, however, the detector can be connected with any wireless communications device that can be paired with the desired electronic device.

The 3DIO system can also be configured to be integrated with any dental station. Thus, the 3DIO system can be configured to connect with, or be moved to, a first dental station and operated to take images of a first patient. Then, the 3DIO system can be removed from the first dental station and then connected with a second (or third, fourth, etc.) dental station to take images of additional patients.

Figure 3:
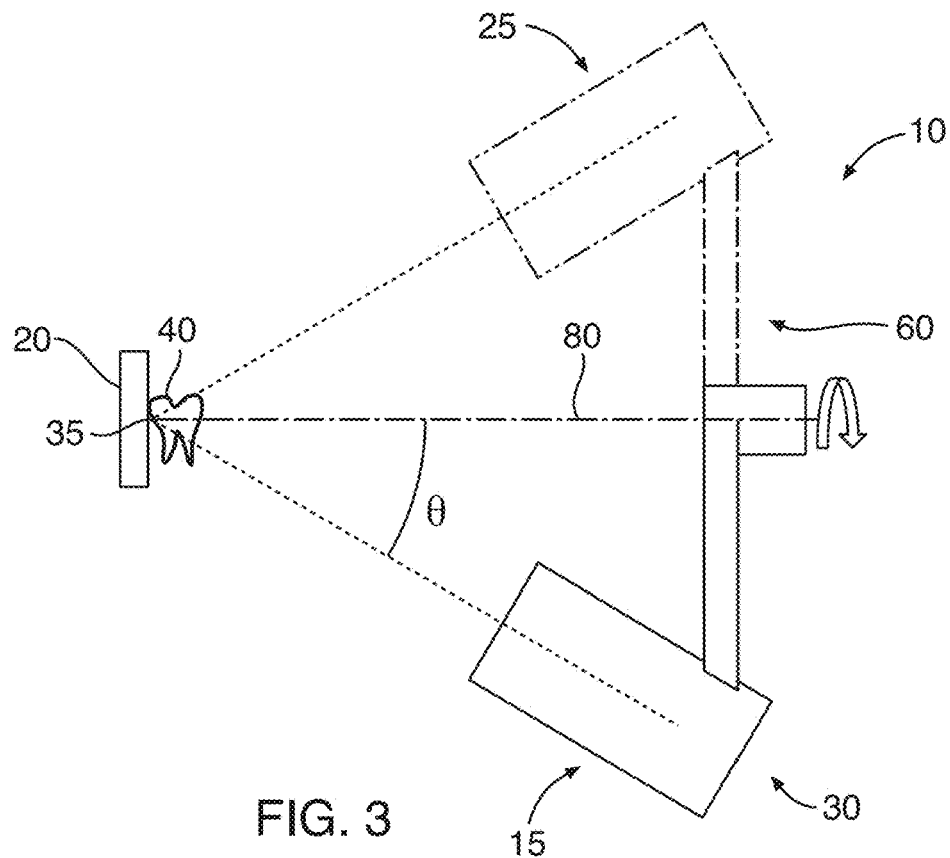
FIGS. 3-4 show some embodiments of the geometry of some components in a 3DIO imaging system.
Figure 4:
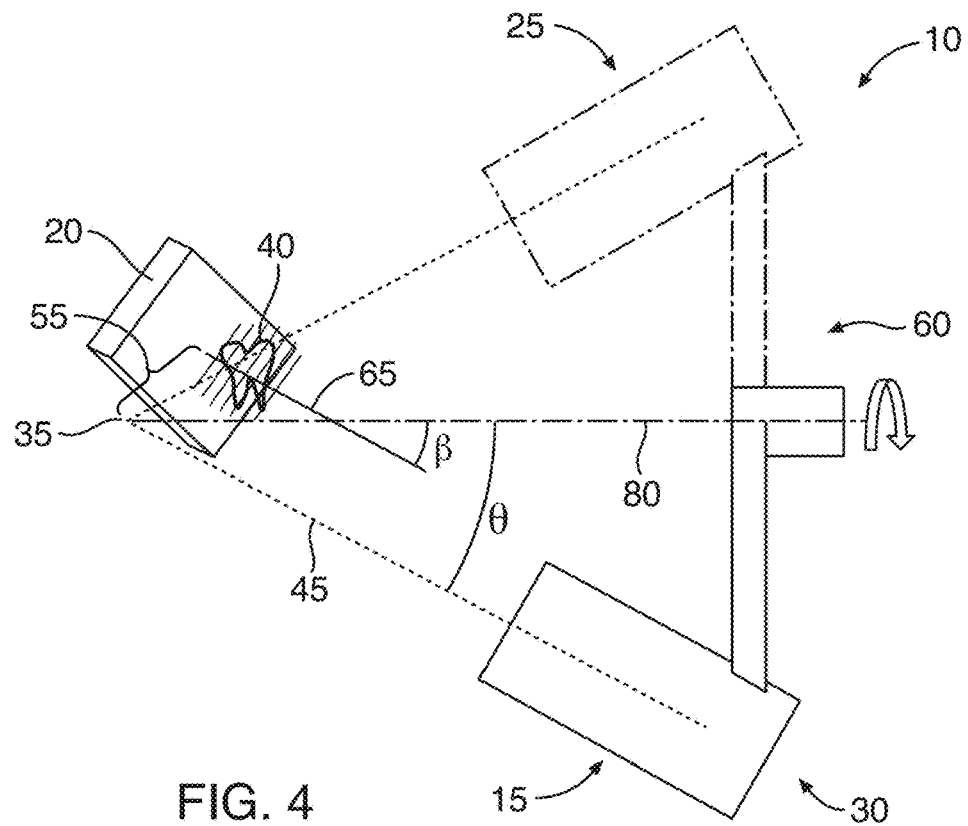

As depicted in FIGS. 3-4, the 3DIO system can also be modified to contain a geometric calibration mechanism. In some configurations, the calibration mechanism uses tooth features as fiducial markers. In other configurations, a geometric calibration could use the image data for calibration as opposed to fiducial markers. FIG. 3 shows an ideal geometry of the 3DIO system 10 with the detector 20 substantially parallel to the tooth 40 and substantially perpendicular to the axis of rotation 80 of the x-ray source 30 from position 15 to position 25. The x-ray beam 45 from the x-ray source 30 impinges on the tooth 40 at an angle θ from the axis of rotation 80 with the axis of rotation located on the center of rotation 35 which is also centered on the detector 20. FIG. 4 shows a real-world example where the alignment of the x-ray source 30 is not perfect with respect to either the tooth 40 or the detector 20. In FIG. 4, the center of rotation 35 is not centered on the detector 20 but is offset by a distance 55. The axis 65 (that is normal to the detector 20) is aligned at an angle θ from the axis of rotation 80. In FIG. 4, the alignment of the rotation axis 80 and the location of the center of rotation 35 with respect to the tooth 40 and the detector 20 must be determined using calibration techniques.

In some embodiments, the mechanical motion of the x-ray source can be partially or fully automated so that little to no operator intervention is required. The motion that is automated would be a constant velocity rotation in most embodiments, as this is the simplest operational mode. Other embodiments, however would use a stop-start approach in which the X-ray source is held stationary during each x-ray exposure and then quickly moved or rotated to the next position. Still other embodiments could use an operational mode in which different rotational velocities are used at different points in the rotation.

The rotation velocity, or the stop-start motion, would be synchronized with the operation of the x-ray source and the detector so that the x-ray source and panel are properly triggered or operated when the x-ray source is at the desired position in its movement or path.

This rotary automation can be accomplished by mounting a light-weight x-ray source(s) on a motion gantry that could be enclosed in a single housing. As noted above, the housing would be mounted on a wall-mount arm like modern intra-oral x-ray sources, but there would be no motion of the housing itself. The partially or fully automated system will allow the operator to collect 3D images with a technique that is simple for the operator to activate so that the operator and the patient experience are comparable to the experience and technique of conventional single 2D radiographs. Ideally, the entire imaging sequence would be activated by pushing a single button or issuing a single command to a computer control system.

Using the partial or full automation of the movement of the x-ray source allows the 3DIO systems to operate on a substantially continuous basis. The x-ray source may pause only long enough to provide the desired amount of x-rays before moving again, or it may be allowed to move continually. In most configurations, the x-ray source need only pause about 10 ms to about 40 ms milliseconds to send the x-ray beams toward the tooth. Then, it only takes about 40 ms to about 100 ms milliseconds to re-position the x-ray source within the housing 50 before sending another set of x-ray beams. The x-ray source can be moved and re-positioned as many times as needed. In other words, the imaging process on average can range from about 50 ms to about 140 ms/image taken.

The timing and sequencing of the x-ray exposures required to generate the 2D image data that will be processed into a 3D image needs to be as quick as possible. It is desirable that the entire process be completed within a period of from about 5 seconds to 10 seconds, with shorter times being preferred for reasons of patient comfort and because a short time makes it easier for the patient to remain motionless during the imaging process. For example, if the imaging sequence needs to be complete within 6 seconds and a total of 24 images are needed within that 6 seconds, the 3DIO system will take 4 images per second. The x-ray source within the housing would need to complete nearly one complete rotation during those 6 seconds, or have a rotational speed of approximately 10 rpm. Since the x-ray source can be pulsed at full power for 10 ms to 20 ms, it leaves approximately 230 ms to 240 ms available for the x-ray detector to read out the image data and prepare to receive the next x-ray pulse, which would occur every 250 ms at a different position of the x-ray source and thus generate the next 2D image. Thus, the entire imaging process for a tooth can be completed quickly (i.e., less than 5-10 seconds) so that motion of the patient does not affect the imaging process, or a simple patient stabilization device (i.e., a chin rest) is sufficient to control patient motion.

If needed to image another tooth, the housing 50 and detector located within the patient's mouth can then be moved to another position. After the housing and detector have been re-positioned, the imaging of the additional tooth can proceed in similar manner as described above. This process can be repeated to image as many teeth as desired.

Using the 3DIO systems described herein allows the operator to drastically reduce the time needed to take the multiple 2D images and use them to render the 3D image. Typically, the process for rendering the 3D images using the multiple 2D images can take less than about 120 seconds. In other embodiments, this time can range from about 30 seconds to about 90 seconds. Given the time needed to take the 2D radiographic images described above, the complete process for taking the 2D images and creating the 3D images can range from about 40 seconds to as long as 100 seconds or even as long as 140 seconds.

As described, the 3DIO system can create a 3D image by capturing a first 2D radiographic image of the tooth at a first angle, moving the position of the x-ray source to take another image from a different angle, and then using a reconstruction algorithm to render a 3D image from the two 2D radiographic images. In many configurations, more than two 2D radiographic images will be used to create the 3D images. In some embodiments, the number of 2D radiographic images can range anywhere from 3 to over 1000 images. In other embodiments, the number of 2D radiographic images can range anywhere from 6 to over 32 images. In yet other embodiments, the number of 2D radiographic images can range anywhere from 9 to 24 images. The actual number of images that are used will vary from one situation to the next, depending on the time available and the resolution required in the 3D image. The more 2D radiographic images that are used, the higher the resolution of the 3D image but the longer the imaging procedure will take since the x-ray source has to move from position to position, the higher the radiation dose to the patient, and the more time will be required for the 3D image calculations. On the other hand, the fewer 2D radiographic images that are used, the lower the resolution of the 3D image but the quicker the imaging process can be.

Figure 5:
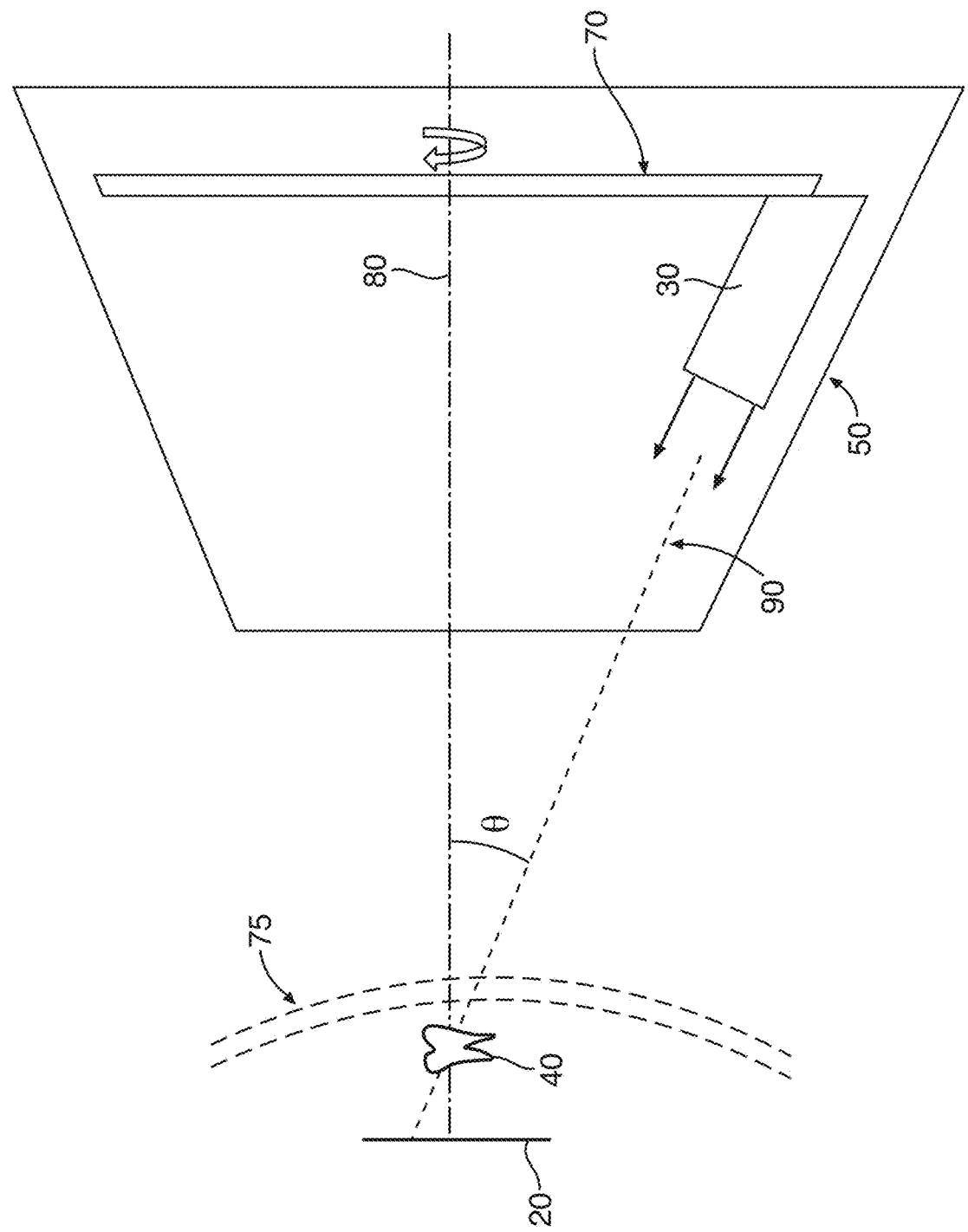
FIGS. 5-6 show some embodiments of the movement of the x-ray source in a 3DIO imaging system.
Figure 6:
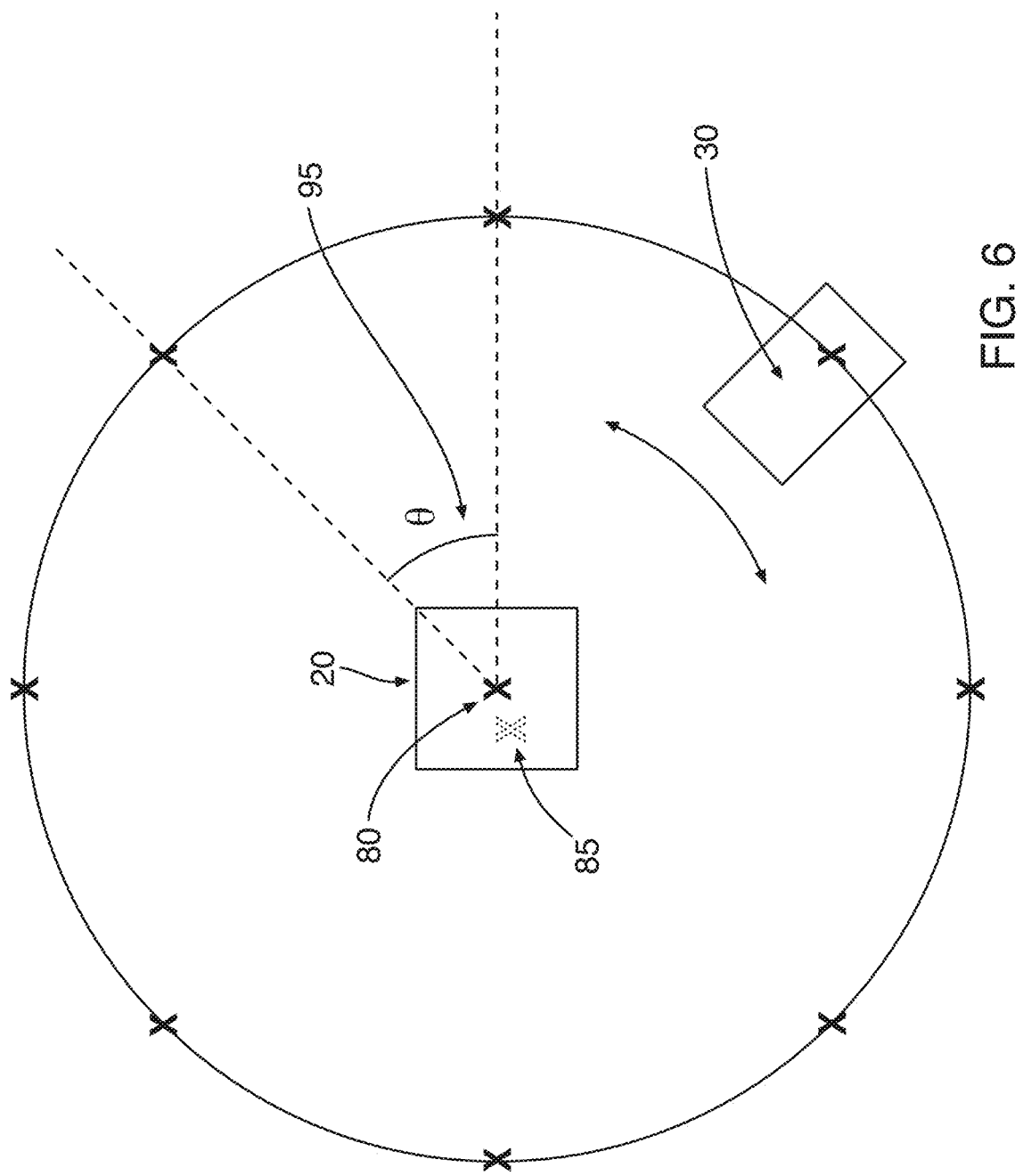

The x-ray source can be moved (or rotated) around any increment from an angle of about 0 degrees to about 360 degrees on a circle located in a plane approximately parallel to the detector 20 located behind a patient's cheek 75, as shown in FIGS. 5-6. The angle θ can be arbitrary and can range from any value near 0 degrees to near 180 degrees depending on what angle will provide the best 3D image quality. In these embodiments, the housing 50 hides the mechanical components from view, as well as being part of the mechanical structure that supports the x-ray source, motors, and other elements that enable the x-ray source 30 to rotate around axis 80. In FIGS. 5-6, unlike CBCT processes where the x-ray source horizontally rotates around the patient's head, the x-ray source 30 rotates in a circle in a plane that is substantially parallel to the longitudinal axis of the tooth 40 and located on just one side of the patient's head. The detector 20 is stationary behind the tooth and in some configurations substantially parallel to the longitudinal axis of the tooth. So the x-ray source 30 can be rotated around an axis of rotation 80 that is approximately perpendicular to the plane of the detector so that the x-ray source itself rotates in a plane approximately parallel to the plane of the detector using mechanical gantry 70. As shown in FIG. 6, the x-ray source 30 is rotated around the axis of rotation 80 at a rotational velocity V that is not necessarily constant. The angle 95 shows the angular displacement between image acquisition points ("X") that are spread evenly around the circle. There may be any number of images taken. The position of each image acquisition point is determined by dividing the circle into a number of equal segments to provide the number of images desired. Alternatively, the image acquisition points may not all be distributed equally on the circle, but a substantial portion of the total number of images desired must be distributed around a substantial portion of the circle so that a number of images are obtained at angles 95 that are significantly different for each image are obtained. The x-ray source 30 does not necessarily physically stop for the image acquisition, but rather is pulsed at each image acquisition point. Alternatively, the X-ray source 30 may be momentarily paused at each image acquisition point if x-ray source motion during the exposure is judged to be undesirable. The axis of rotation 80 can be centered on the detector 20 and is ideally parallel to the detector normal. But since this will be difficult to fully achieve in practice, a reconstruction algorithm can incorporate correction methods to enable a quality reconstruction. In some configurations, the axis of rotation 80 is not necessarily fixed on the center of the detector 20, but may be displaced from the center as depicted by the alternate location 85 of the axis of rotation 80. Indeed, the x-ray source 30 can rotate through any portion of the circular arc that ranges from 0 to about 360 degrees in that plane which is substantially vertical if the patient's tooth is oriented in a vertical direction. So using the 3DIO systems described herein, the operator could conceivably take 2D images from any location in the parallel plane by changing the location in polar coordinates, theta and phi, rather than X and Y Cartesian coordinates. Alternatively, this same set of locations could be described using circular coordinates in the plane consisting of the radius R and the angle theta. Thus, the 3DIO system is different from conventional tomosynthesis for mammography or chest x-rays where the source moves in a limited arc within a plane that is perpendicular to the face of the detector.

If the x-ray source moves in this manner (i.e., in a substantially circular motion and substantially constant rotational speed), its apparent instantaneous speed of movement in the X and Y directions as defined by the detector array will be sinusoidal, since it is moving in a circle. The X and Y sinusoidal movements are also 90 degrees out of phase, so that when the speed in the X direction is at a maximum, the Y movement is zero, and vice versa. To obtain the maximum resolution in the resulting 3D image, keeping track of where the X-ray source is in its motion and weighting the pixels appropriately for X and Y resolution during the image reconstruction so that the images taken when the X-ray source is showing zero, or small amounts, of X-displacement are given greater value in defining the X-resolution of image features, and the same approach for the Y-resolution of image features, will help the reconstruction algorithm reduce or eliminate motion blur caused by a continuous motion of the x-ray source during the 2D image capture process.

There exist a number of 3D reconstruction systems or methods known in the art. Most of these systems or approaches have failed in practice since the operator was required to manually reposition the x-ray source and take each 2D projection just as with a standard intra-oral radiograph. The substantial time required for an operator to manually take 9 to 15 intra-oral radiographs, along with the patient discomfort inherent in such a process, combined with the extended time required for 3D reconstruction process, made use of these systems or methods impractical for most dental procedures.

The 3DIO system uses an image capture process that is much quicker. This is largely due to the automated image capture that is enabled by simplifying the x-ray source motion by confining it to a circular motion in a plane that is substantially parallel to the detector and leaving the detector in the same position for each image. This method makes it possible to automate the image capture process.

Advancements in the parallel computational power of Graphics Processing Unit (GPU) hardware have allowed clinical implementation of iterative and statistical reconstruction techniques for tomography and tomosynthesis. These iterative techniques use variational-based methods to maximize a likelihood function describing the probability of the reconstructed image given detector measurements. These advancements, when combined together with the automated capture of the 2D image data, make it practical to consider a 3DIO system as described that offers an ease of use and work flow that is comparable to standard 2D dental X-rays.

The use of these iterative techniques in the generation of the 3D image offer several advantages. First, these techniques are robust to missing data and arbitrary projection scans (such as scans with non-standard geometries). Second, these techniques directly model the physics and noise characteristics of the imaging system. And third, these techniques allow the use of a prior probability of the 3D reconstructed image to reduce the time required for the algorithm to converge on the correct high-resolution image.

The 3DIO systems described herein exhibit several helpful features. One helpful feature of the 3DIO systems includes the ability to obtain high resolution 3D images while employing x-ray dose minimization schemes. Prior to the 3DIO systems described herein, to obtain a 3D image with a resolution of 100 microns or better typically required x-ray dosages of ranging from 300 µSv to 1,0000 µSv. The 3DIO systems described herein allow the operator to get a similar resolution with much smaller dosages ranging from about 10 µSv to about 45 µSv.

Another helpful feature includes the increased imaging efficacy. This efficacy can be achieved since the system interfaces and synchronizes low-power x-ray tubes with CMOS sensors and collects 2D images from multiple angles, thereby reducing the number of images needed to achieve diagnostic quality images by optimizing the spatial resolution, noise, contrast-to-noise ratio, and geometric accuracy. This will provide benefits to the practicing dentist by providing better diagnostic images of teeth with cracks, interproximal caries, overlapping roots (when viewed in 2D radiographs), and other anomalous anatomy and diagnostic challenges in dentistry.

The 3DIO systems described herein can perform comparably to tuned aperture computed tomography (TACT) systems more rapidly and at lower cost. TACT systems employ dental tomosynthesis with intra-oral sensors that can be as accurate as CBCT in detecting some tooth fractures. Indeed, commercial software for the 3D reconstruction of tomosynthesis data using TACT has been developed. Unfortunately, this approach failed in clinical practice, primarily because the operator was required to manually reposition the x-ray source and take each 2D image similar to a standard intra-oral radiograph. This illustrates the importance and value of the 3DIO imaging approach which avoids the requirement that the x-ray source be manually repositioned.

An attractive feature of the 3DIO systems described herein is its adaptability for a dental practice. Dental imaging must meet a number of constraints to be adopted into a dental practice in addition to just providing a reduced x-ray dosage and improved resolution over the existing CBCT approaches. CBCT procedures, and some conventional 3D dental imaging systems and approaches, have not been successful in achieving acceptance into standard dental practice because they impose unacceptable burdens on the patient and on the practice of dentistry. These burdens include issues of unacceptable monetary cost; unacceptable or unattractive burdens born by the patient such as personal discomfort, x-ray dose, and time at the dentist to receive treatment; and disruption of the work flow in the dental practice. Each of these issues needs to be addressed and resolved in order to create a 3D dental imaging system that will be of interest to the majority of dental practices.

By way of explanation, a typical work flow in a dental practice for taking 2D images of a tooth is as follows. The dental technician or dentist will insert a digital imaging device into the patient's mouth that is sized to fit with some level of comfort into the mouth. The x-ray source is then positioned external to the patient's mouth with the x-ray radiation aimed at the detector appropriately, and then the x-ray source is triggered and the image is obtained. The entire process to obtain a single x-ray image typically takes 30-60 seconds, with additional images requiring less additional time because the required equipment is already in the approximately correct position.

To achieve a similar work-flow for a 3D dental image, several requirements should be met. The first requirement is that the x-ray source must be low weight and relatively small so that it may be mounted on the wall similar to standard dental x-ray equipment and readily and easily positioned as necessary. Alternatively, it may be mounted in other ways that provide for the appropriate positioning. The second requirement is that the intra-oral detector must be similar in size, feel, patient comfort level, etc. to existing intra-oral detectors. The third requirement is that the entire imaging process must be able to be completed within a relatively short period of time such as 5 to 10 seconds. The fourth requirement is that positioning of the x-ray source with respect to the patient and the intraoral detector be easily and quickly accomplished.

As well, a typical 2D dental image is obtained without any constraints on the patient's movement or position other than a verbal request to remain motionless while the image is taken. A 3D dental imaging process that imposes significant discomfort on the patient by imposing a head restraining device or by requiring that a large x-ray source device be positioned next to the patients head would cause significant patient discomfort and consequent patient resistance to the use of 3D imaging as standard practice.

Meeting the need for a similar level of patient comfort imposes the following constraints on the 3D dental imaging systems. First, in order to avoid any kind of head motion restraint that would be more uncomfortable than a simple chin rest or similar approach, the 3D imaging process must be accomplished quickly, on the order of less than 5 seconds, and certainly less than 10 seconds. Since the number of 2D images required for an accurate 3D rendering is typically between about 15 images and 50 images, the 2D image capture rate needs to be at least on the order of 5 or more images per second.

The second constraint is that the x-ray source needs to be small and appear to be similar in size and shape to existing x-ray sources with which patients are familiar. And since the imaging process must be completed quickly, and the x-ray source must move in an arc, circle, or some other geometric path in order to obtain the required 2D images, it is necessary that the x-ray source be light weight in order to simplify the issues of managing the required mechanical motion, counterweights, and other engineering concerns, and also physically small. It is desirable that the x-ray source weigh itself less than 1.5 Kg, and certainly less than 5 Kg, and that it be less than about 20 cm in length, about 8 cm in width, and 8 cm in height.

A third constraint concerns the speed and capability of the computer processor that performs the mathematically complex calculations required to reconstruct a 3D image. It is helpful that the 3D calculations be completed within a short time after the 2D image data is gathered, again in order to meet the requirements on patient comfort and acceptance, and to fit within the workflow of the typical dental practice. It is expected that this requirement will become easier to meet as computer technology continues to advance, but the time required to present the 3D data to the dentist should not be more than about 90 seconds.

Finally, meeting the challenge of monetary cost imposes constraints on the technology that can be implemented in the 3D imaging system. Some approaches use an x-ray source array for 3D dental imaging, but this imposes significant costs because it does not take advantage of the existing, inexpensive, well developed, reliable vacuum tube x-ray sources. Utilizing an advanced x-ray source array, while being technically attractive, offers little advantage to the dental practitioner or to the dental patient in terms of image quality, x-ray dose, or other important performance factors over the lower-cost conventional x-ray source that can easily be moved and pulsed rapidly to generate the required 2D x-ray images within the desired time limitations.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An x-ray imaging system, comprising:
    an x-ray source attached to a motion gantry configured to move the x-ray source in a circular motion to multiple positions on a first side of an object to be imaged;
    a counterweight attached to the motion gantry;
    a substantially stationary x-ray detector array located on an opposite side of the object than the x-ray source, the detector array synchronized with the x-ray source to capture two dimensional (2D) images of the object when the x-ray source is located in the multiple positions; and
    a processor configured to accept the 2D images and reconstruct a three-dimensional image.

2. The system of claim 1, wherein the object is a single tooth or multiple teeth.

3. The system of claim 1, wherein the counterweight comprises another x-ray source.

4. The system of claim 1, wherein the processor is configured to use tomosynthesis algorithms to reconstruct the 3D image.

5. The system of claim 4, wherein the tomosynthesis algorithms comprise an iterative process.

6. The system of claim 1, wherein the movement of the x-ray source is partially or completely automated.

7. The system of claim 1, wherein the system collects up to 1000 2D images.

8. The system of claim 1, wherein the system collects 6 to 32 2D images.

9. The system of claim 1, wherein the system collects 9 to 24 2D images.

10. The system of claim 1, wherein the system repositions the x-ray source between the multiple positions within about 40 ms to about 100 ms.

11. A method for making a three dimensional image of an object, comprising:
- providing an x-ray source on a motion gantry on a first side of an object to be imaged;
- providing a counterweight attached to the motion gantry;
- positioning a substantially stationary x-ray detector array on an opposite side of the object;
- moving the x-ray source in a circular motion to multiple positions on that first side of the object;
- collecting multiple two dimensional (2D) images of the object when the x-ray source is located in the multiple positions; and
- reconstructing a three-dimensional (3D) image using the multiple 2D images.

12. The method of claim 11, wherein the object is a single tooth or multiple teeth.

13. The method of claim 11, wherein the processor is configured to use tomosynthesis algorithms to reconstruct the 3D image.

14. The method of claim 13, wherein the tomosynthesis algorithms comprise an iterative process.

15. The method of claim 11, wherein the counterweight comprises another x-ray source.

16. The method of claim 11, wherein the movement of the x-ray source is partially or completely automated.

17. The method of claim 11, wherein the system collects up to 1000 2D images.

18. The method of claim 17, wherein the system collects 6 to 32 2D images.

19. The method of claim 11, wherein the system re-positions the x-ray source between the multiple positions within about 40 ms to about 100 ms.

20. The method of claim 12, wherein the entire process for image capture and 3D reconstruction for a single tooth can be completed in less than about 10 seconds.

21. The method of claim 12, wherein the entire process for image capture and 3D reconstruction for a single tooth can be completed in less than about 5 seconds.

* * * * *